United States Patent
Schumacher et al.

(10) Patent No.: US 11,384,325 B2
(45) Date of Patent: Jul. 12, 2022

(54) SINGLE-USE BIOREACTOR PORT WITH MULTIPLE SENSORS

(71) Applicant: Rosemount Inc., Shakopee, MN (US)

(72) Inventors: Mark S. Schumacher, Minneapolis, MN (US); Chang-Dong Feng, Long Beach, CA (US)

(73) Assignee: Rosemount Inc., Shakopee, MN (US)

( * ) Notice: Subject to any disclaimer, the term of this patent is extended or adjusted under 35 U.S.C. 154(b) by 358 days.

(21) Appl. No.: 15/084,911

(22) Filed: Mar. 30, 2016

(65) Prior Publication Data

US 2016/0298068 A1    Oct. 13, 2016

Related U.S. Application Data (60) Provisional application No. 62/146,460, filed on Apr. 13, 2015.

(51) Int. Cl.
| | | |
|---|---|---|
| *C12M 3/00* | (2006.01) | |
| *C12M 1/00* | (2006.01) | |
| *B01L 3/00* | (2006.01) | |
| *C12M 1/34* | (2006.01) | |

(52) U.S. Cl.
CPC .......... *C12M 23/14* (2013.01); *C12M 23/28* (2013.01); *C12M 41/26* (2013.01); *C12M 41/34* (2013.01)

(58) Field of Classification Search
CPC ....... C12M 23/14; C12M 23/40; C12M 23/28
See application file for complete search history.

(56) References Cited

U.S. PATENT DOCUMENTS

| | | |
|---|---|---|
| 7,924,017 B2 | 4/2011 | Ammann et al. |
| 8,123,397 B2 | 2/2012 | Baumfalk et al. |
| 8,252,582 B2 | 8/2012 | Baumfalk et al. |
| 8,304,231 B2 | 11/2012 | Roll |
| 8,640,560 B2 | 2/2014 | Burke |
| 8,900,855 B2 | 2/2014 | Feng et al. |
| 8,828,202 B2 | 9/2014 | Feng |
| 9,267,100 B2 | 2/2016 | Selker et al. |

(Continued)

FOREIGN PATENT DOCUMENTS

| | | |
|---|---|---|
| DE | 102009037345 A1 | 12/2010 |
| EP | 2363704 A1 | 9/2011 |

(Continued)

OTHER PUBLICATIONS

International Search Report and Opinion for PCT/US2016/024869, dated Jul. 12, 2016, Filed Mar. 30, 2016. 11 pages.

(Continued)

*Primary Examiner* — Nathan A Bowers
(74) *Attorney, Agent, or Firm* — Christopher R. Christenson; Kelly, Holt & Christenson PLLC (57) ABSTRACT

A bioreactor vessel is provided. The bioreactor vessel comprises a bioreactor bag wall having an interior side and an exterior side and an aperture extending from the interior side to the exterior side, wherein the interior side is configured to contact and house a reaction mixture. The bioreactor vessel also comprises a port mounted proximate the aperture, the port including a flange fixedly attached to the bioreactor bag, such that a fluidic seal is maintained along a circumference of the flange. The bioreactor vessel also comprises a plurality of sensors disposed within the port.

15 Claims, 5 Drawing Sheets

(56) References Cited

U.S. PATENT DOCUMENTS

| | | | |
|---|---|---|---|
| 2001/0028865 A1* | 10/2001 | Cummings | G01N 27/283 |
| | | | 422/560 |
| 2004/0027912 A1 | 2/2004 | Bibbo et al. | |
| 2005/0163667 A1 | 7/2005 | Krause | |
| 2006/0051874 A1* | 3/2006 | Reed | G01N 21/6428 |
| | | | 436/163 |
| 2006/0131765 A1* | 6/2006 | Terentiev | B01F 3/04248 |
| | | | 261/93 |
| 2010/0255526 A1* | 10/2010 | Braet | B01F 3/04262 |
| | | | 435/29 |
| 2011/0124035 A1* | 5/2011 | Broadley | C12M 41/00 |
| | | | 435/29 |
| 2012/0178151 A1 | 7/2012 | Feng et al. | |
| 2012/0240686 A1 | 9/2012 | Blomberg et al. | |
| 2013/0145818 A1 | 6/2013 | Allgauer et al. | |

FOREIGN PATENT DOCUMENTS

| | | | |
|---|---|---|---|
| JP | 2005-002109 A | 1/2005 | |
| JP | 2012-200258 A | 10/2012 | |
| WO | 2010145735 A2 | 12/2010 | |
| WO | 2014190357 A1 | 11/2014 | |
| WO | 20150067541 A1 | 1/2015 | |

OTHER PUBLICATIONS

Office Action dated Apr. 25, 2018, for Russian Patent Application No. 2017132652, 8 pages including English Translation.
First Examination Report, dated Feb. 22, 2018, for Australian Patent Application No. 2016247845, 3 pages.
Office Action, dated Jan. 25, 2018, for Russian Patent Application No. 2017132652, 11 pages including English translation.
Office Action dated May 25, 2018, for Canadian Patent Application No. 2979723, 3 pages.
Second Examination Report dated Jan. 3, 2019, for Australian Patent Application No. 2016247845, 4 pages.
Office Action dated Nov. 27, 2018, for Chinese Patent Application No. 201680000910.7, 18 pages including English translation.
First Office Action dated Sep. 4, 2018, for Japanese Patent Application No. 2017-547160, 10 pages including English translation.
Extended EPO Search Report dated Nov. 2, 2018, for European Patent Application No. 16780440.0, 7 pages.
Second Japanese Office Action dated Jul. 30, 2019 for Japanese Patent Application No. 2017-547160. 7 pages including English translation.
Second Office Action dated Apr. 18, 2019 for Chinese Patent Application No. 2019041501771040, 19 pages including English translation.
Canadian Office Action dated Feb. 4, 2019, for Canadian Patent Application No. 2979723, 3 pages.
Rejection Decision for Chinese Patent Application No. 201680000910.7 dated Sep. 29, 2019, 19 pages with English Translation.
Rejection Decision dated Jul. 6, 2021, for Japanese Patent Application No. 2019-010234, 11 pages including English translation.
First Examination Report dated Sep. 16, 2021, for Indian Patent Application No. 201727029742, 7 pages including English translation.

* cited by examiner

SINGLE-USE BIOREACTOR PORT WITH MULTIPLE SENSORS

CROSS-REFERENCE TO RELATED APPLICATIONS

The present application is based on and claims the benefit of U.S. Provisional Patent Application Ser. No. 62/146,460, filed Apr. 13, 2015, the content of which is hereby incorporated by reference in its entirety.

BACKGROUND

Bioreactors are useful for generating and supporting biological reactions for any number of purposes. Biological reactions can be susceptible to changes in temperature and/or pressure. Moreover, as the biological reaction progresses, the reaction itself may change various parameters within the bioreactor vessel, such as dissolved oxygen content and/or pH. Accordingly, it may be important to monitor a number of variables of the biological reaction.

The life sciences industry is moving from large, capital-intensive facilities made of stainless steel with large clean-in-place (CIP) infrastructure to smaller facilities that use polymer bags or containers functioning as the bioreactors. The bioreactor bag is used once and then disposed. This single-use bioreactor technique significantly reduces the capital cost of the plant. For example, in existing facilities that use stainless steel CIP infrastructure, up to 90% of the cost of operating the facility may be due to the clean-in-place infrastructure, including very high end instrumentation designed to withstand a steam cleaning cycle. By moving to disposable, single-use, bioreactor bags, the CIP portion of the capital can be eliminated and the facility can be more flexible and much smaller, which, in turn, allows the production of smaller batches that are needed for more targeted drug therapies and other smaller-scale applications.

SUMMARY

A bioreactor vessel is provided. The bioreactor vessel comprises a bioreactor bag wall having an interior side and an exterior side and an aperture extending from the interior side to the exterior side, wherein the interior side is configured to contact and house a reaction mixture. The bioreactor vessel also comprises a port mounted proximate the aperture, the port including a flange fixedly attached to the bioreactor bag, such that a fluidic seal is maintained along a circumference of the flange. The bioreactor vessel also comprises a plurality of sensors disposed within the port.

DETAILED DESCRIPTION OF ILLUSTRATIVE EMBODIMENTS

Figure 1:
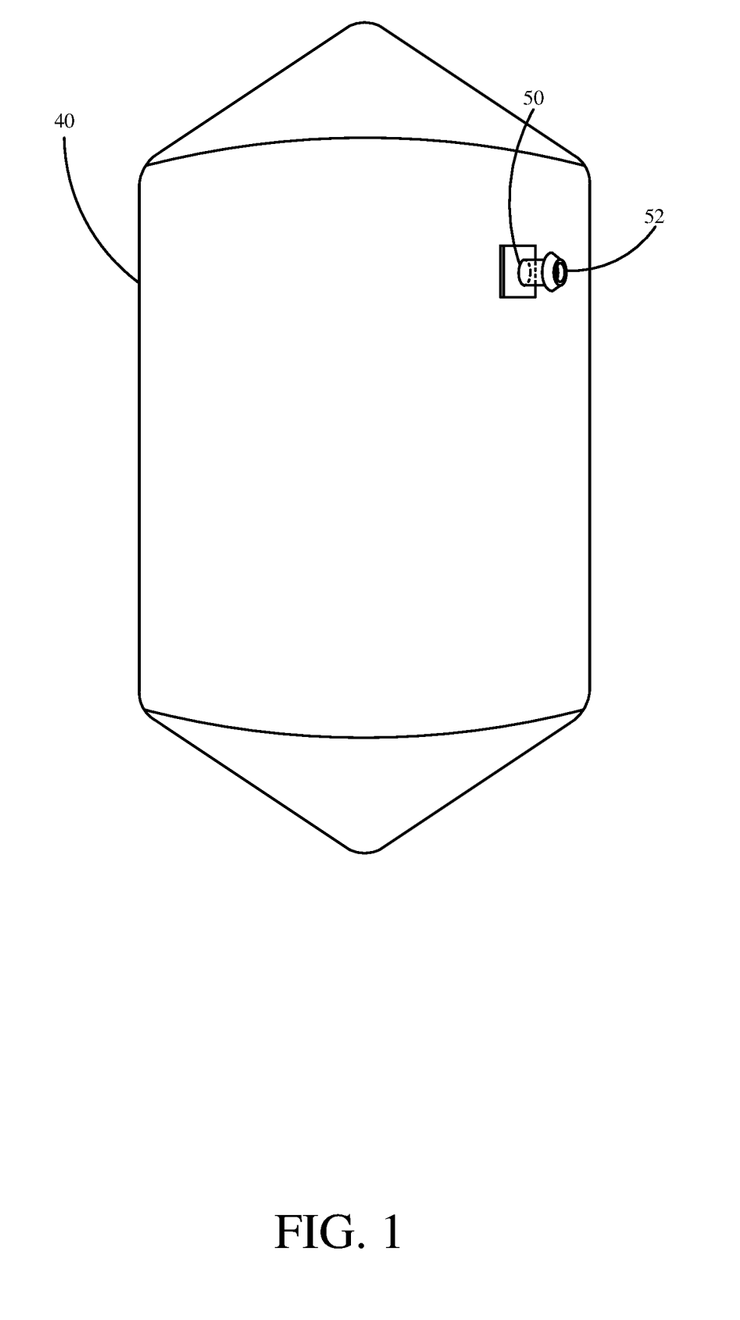
FIG. 1 illustrates an example of a disposable bioreactor bag, with which embodiments of the present invention are particularly useful.

FIG. 1 illustrates an example of a disposable bioreactor bag, with which embodiments of the present invention are particularly useful. Single-use, or disposable, reaction chambers are known in the art, and are frequently used for biologic reactions, for example.

Use of single-use bioreactor 40, greatly reduces the capital cost required for an industrial facility while providing sterile reaction chambers. Single-use bioreactor chambers 40 often are attached to a variety of sensing equipment, through a number of ports.

During the manufacturing process of a single-use bioreactor 40, ports are typically fixed to the single-use bioreactor/mixer bags to create a closed system. In addition to providing access for sensor equipment, the ports may also be used as inlet/outlet of the bag. In many cases, the bioreactor may contain two pH sensors, two dissolved oxygen (DO) sensors, a temperature sensor, and a conductivity sensor. Each sensor typically has its own port that is separately mounted on the bioreactor bag.

Maintaining the integrity of the closed system is one of the biggest challenges of the single-use bioreactor bag manufacturing process. Most of the integrity failures are caused by the process of fixing ports to vessel 40. Manufacturing processes, then, may have to sacrifice integrity, or produce a chamber with greater sensor access. Therefore, methods and manufactures that minimize the number of ports while allowing for sufficient process monitoring will provide an improved, more reliable bioreactor over those with multiple ports.

In accordance with embodiments of the present invention, a single-use bioreactor bag, for example bioreactor 40 as illustrated in FIG. 1, is provided with a single port 50 that is configured to receive, through an inlet 52, any one of a plurality of sensors, and/or a single multi-sensor configured to sense a plurality of process variables. A bioreactor 40 with a single port 50 that is as capable of providing all of the sensor signals desired by an operator as a multiport bioreactor 10, without the creation of multiple ports during the manufacturing process, reduces the risk of creating a leakage during the manufacturing process of fixing the port to the bag.

Port 50 may, in one embodiment, be configured to accommodate one or more multi-sensors configured for measuring any of pH, dissolved oxygen, conductivity, temperature, and/or other relevant process variables. In another embodiment, port 50 is configured to accommodate one or more single-variable sensors each configured to sense a relevant process variable. Embodiments of the present invention reduce the number of ports fixed on the single-use bioreactor/mixer. As a result, the manufacturing process of the single-use, single-port bioreactor 40 is simplified and the chance of failure due to leakage is minimized.

Figure 2A:
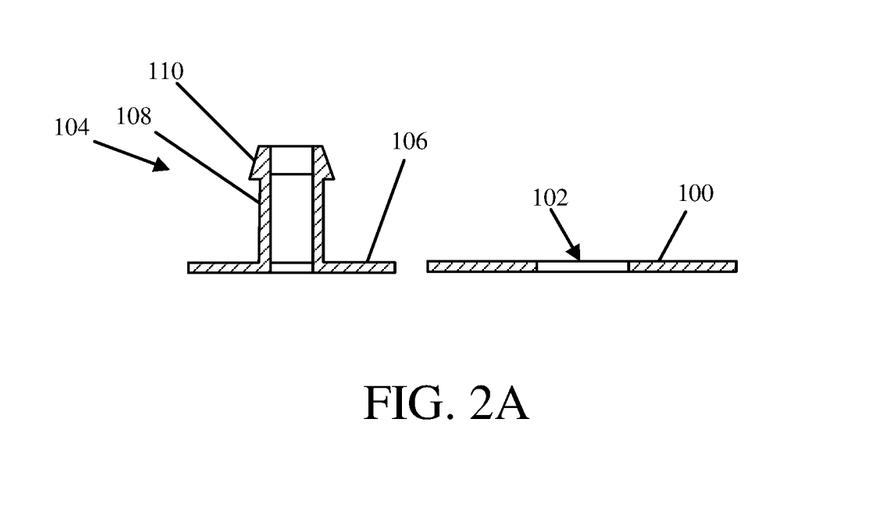
FIGS. 2A and 2B are cross-sectional side and top plan views, respectively, of a single-use bioreactor bag wall and sensor port in accordance with an embodiment of the present invention.
Figure 2B:
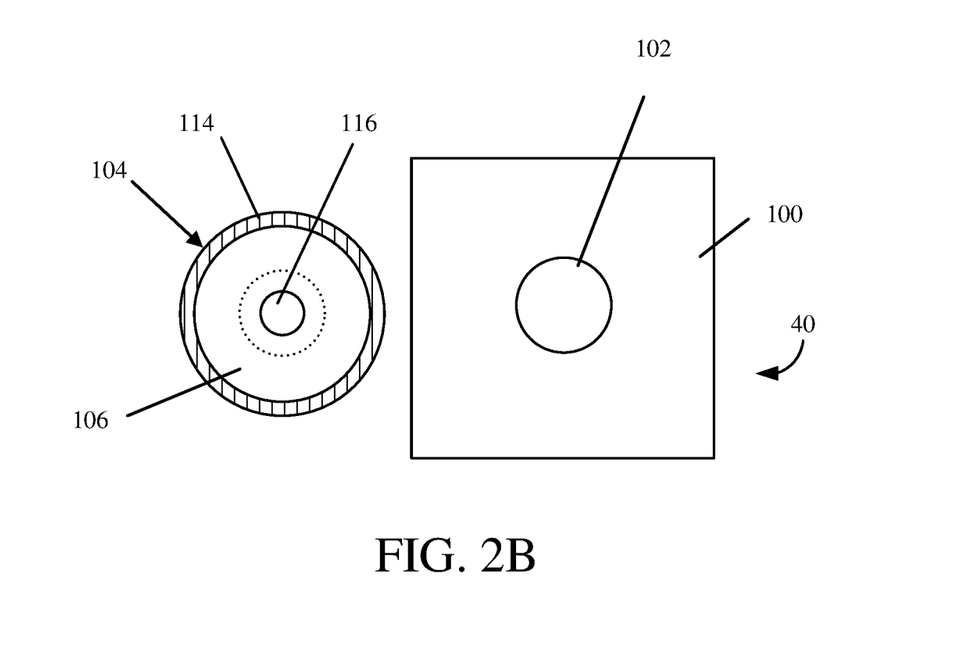

FIGS. 2A and 2B are cross sectional side and top plan views, respectively, of a port 104 and bag wall 100 of a single-use bioreactor, for example bioreactor 40, in accordance with an embodiment of the present invention. Wall 100 of bioreactor bag 40 includes an aperture 102 that is sized, in one embodiment, to allow neck portion 108 and tubing barb 110 of port 104 to pass through. Each of port 104 and wall 100 are, in one embodiment, formed of a polymeric material that facilitates bonding, such as thermal welding. Port 104 includes a flange 106 that is configured to bear against a surface of wall 100 such that wall 100 and flange 106 can be coupled together, for example by an adhesive or thermal welding process.

Figure 3A:
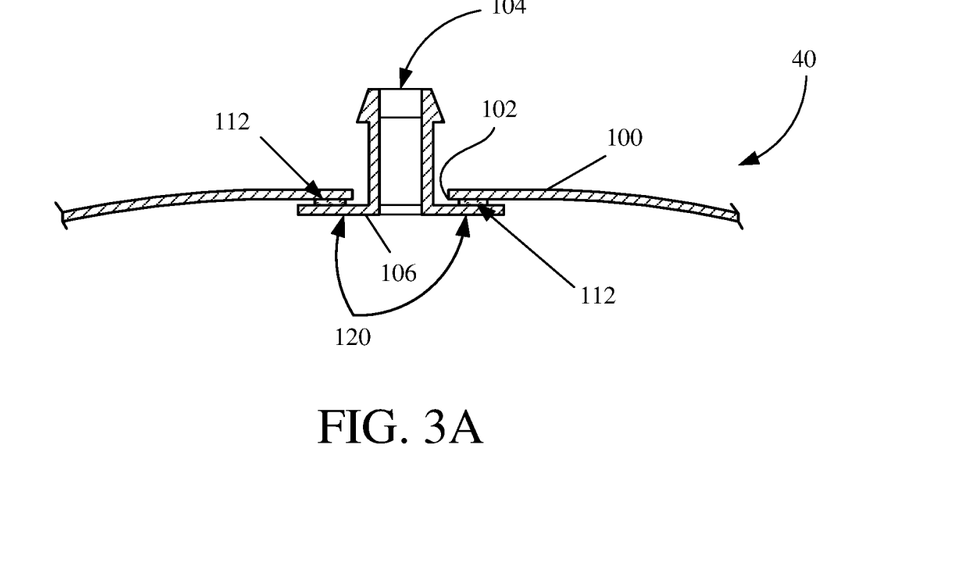
FIGS. 3A and 3B are cross-sectional side and top plan views, respectively, of a single-use bioreactor bag wall and sensor port attached together in accordance with an embodiment of the present invention.

In one embodiment, neck 108 and tubing barb 110 pass through aperture 102 such that flange 106 contacts an inner surface of wall 100, for example as illustrated in FIG. 3A which is described in further detail below. Flange 106 and bag wall 100 can be coupled together in any suitable manner including, in one embodiment, the use of adhesives configured to bind flange 106 and bag wall 100, creating a seal that retains a fluid within bioreactor 40. For example, a water-resistant adhesive is used with bioreactor bags 40 configured to conduct water-based reactions. In another embodiment, oil-resistant adhesives, or other adhesives, are used with bioreactor bags 40 configured to accommodate other reaction mixtures.

In another embodiment, flange 106 is fused to wall 100 such that no intervening material boundary layers exist between flange 106 and wall 100. Such fusing can be performed using any suitable techniques such as, in one embodiment, thermal or chemical welding. FIG. 3A, described in further detail below, shows a fusion between flange 106 and wall 100, for example at location 120. A fusion bond creates an extremely robust mechanical connection as well as a highly effective seal, which is particularly important when the interior of the bioreactor 40 must be kept sterile. While adhesive and fusion-based connection mechanisms have been described, other appropriate connection mechanisms are also envisioned in other embodiments.

FIG. 2B is a top plan view of port 104 configured for coupling to wall 100 of a bioreactor bag in accordance with an embodiment of the present invention. In an embodiment where the coupling is accomplished by thermal welding, the region that will undergo thermal welding is indicated at reference numeral 114. Thermal welding can provide a fluid-tight seal for the sensor assembly to the bioreactor bag 40.

Figure 3B:
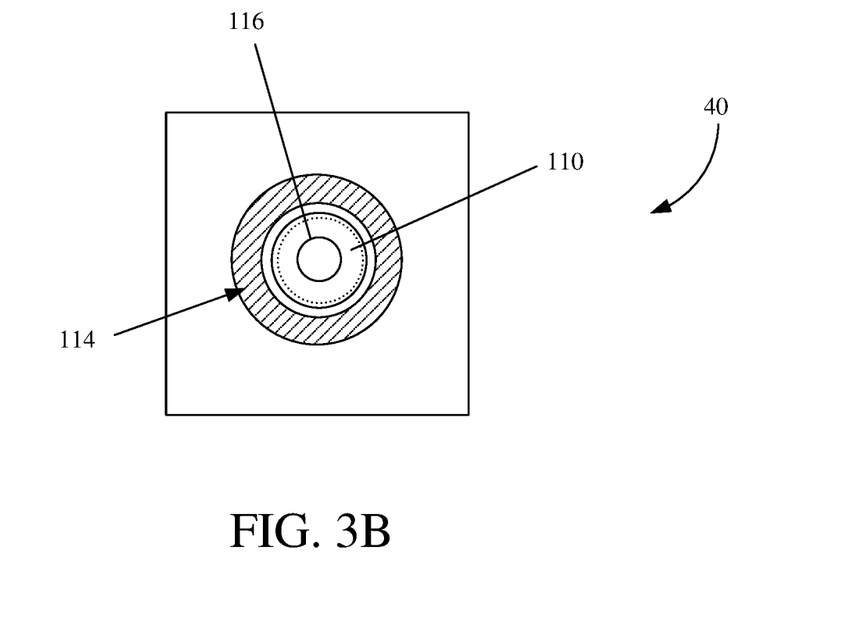

FIGS. 3A and 3B are cross-sectional side and top plan views, respectively, of a single-use bioreactor bag wall and sensor port attached together in accordance with an embodiment of the present invention. As described above, wall 100 and flange 106 are attached, in one embodiment by adhesive. In another embodiment, the attachment is accomplished by thermal or chemical welding. Thermal welding may provide additional advantages as it reinforces the aperture 102 and wall 100 around the port 104, further decreasing the likelihood of leakage. However, in other embodiments, other appropriate attachment mechanisms are envisioned.

FIG. 3A illustrates a cross-sectional side view of a port 104 fixedly attached to wall 100. In one embodiment, port 104 is configured to receive a sensor and provide contact between the received sensor and a mixture within the bioreactor bag 40 such that the sensor can report sensed process variable information.

In one embodiment, attachment point 120 includes an adhesive liner configured to attach, on a first side, to wall 100 and, on a second side, to flange 106. In one embodiment, the adhesive layer 112 may comprise any of a pressure-sensitive adhesive, a hot-melt adhesive, or another reactive or non-reactive adhesive formulation. In one embodiment, the adhesive layer 112 comprises a multi-component adhesive formed by crosslinking, for example using any of acrylics, urethanes, epoxies, esters, alcohols, etc. In another embodiment, the adhesive layer 112 is formed by a curing process, for example utilizing exposure to radiation, heat, water, or another catalyst. In some embodiments, the adhesive is a natural adhesive. In some embodiments, the adhesive is a synthetic adhesive. In at least one embodiment, the adhesive, and method of application, is selected based on an intended use of the bioreactor 40. For example, the adhesive may be selected such that its components are nonreactive with regard to any of the reactants, solvents, or catalysts bioreactor 40 is configured to house.

In one embodiment, attachment point 120 represents a portion of the flange 106 and wall 100 that have been welded together, for example through a thermal or chemical welding process. Welding may be accomplished, in one example, by heating flange 106 and wall 100 above their respective melting points, such that they fuse into a single portion. In one embodiment, flange 106 and wall 100 comprise the same material and, therefore, have similar melting points. In another embodiment, flange 106 and wall 100 comprise different materials, with different melting points.

FIG. 3B is a top plan view of a single-use bioreactor bag wall and sensor port after an attachment process in accordance with an embodiment of the present invention. In one embodiment, manufacture of a single-use, single-port bioreactor bag, such as bioreactor vessel 40, involves attachment of port 104 to a portion of wall 100 using an attachment mechanism. The attachment mechanism may, in one embodiment, involve an adhesive bonding step. In another embodiment, the attachment mechanism may involve thermal welding, for example along a thermal welding zone 114. Thermal welding zone 114, in one embodiment, completely encircles port 104 such that a seal is created preventing leakage of a reaction mixture from the bioreactor 40. Port 104, as manufactured, includes an aperture 116 configured to allow access directly into the interior of the bioreactor bag 40 by a sensor, even after an attachment step is completed. In at least one embodiment, a sensor assembly having two distinct sensors can be implemented within a tube that can be coupled directly to tubing barb 110, for example as described in further detail with regard to FIGS. 4A and 4B.

Figure 4A:
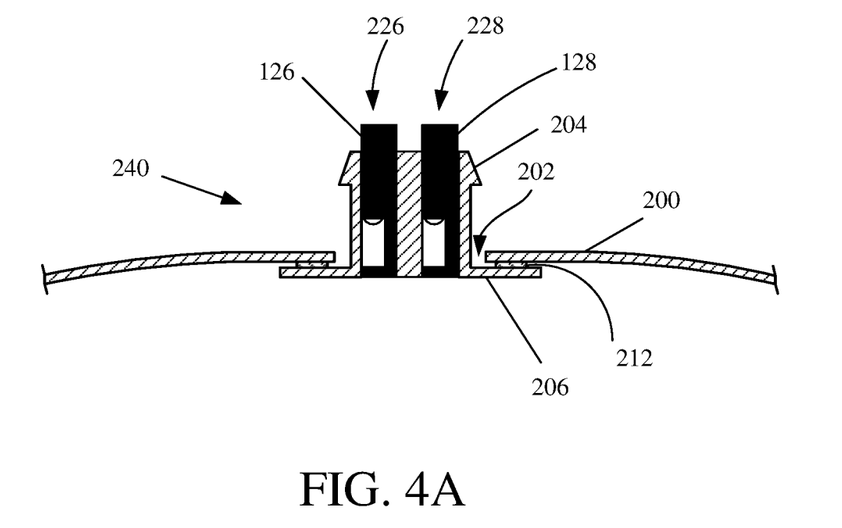
FIGS. 4A and 4B are cross-sectional side and top plan views, respectively, of a plurality of sensors mounted to a single-use bioreactor through a port in accordance with an embodiment of the present invention.
Figure 4B:
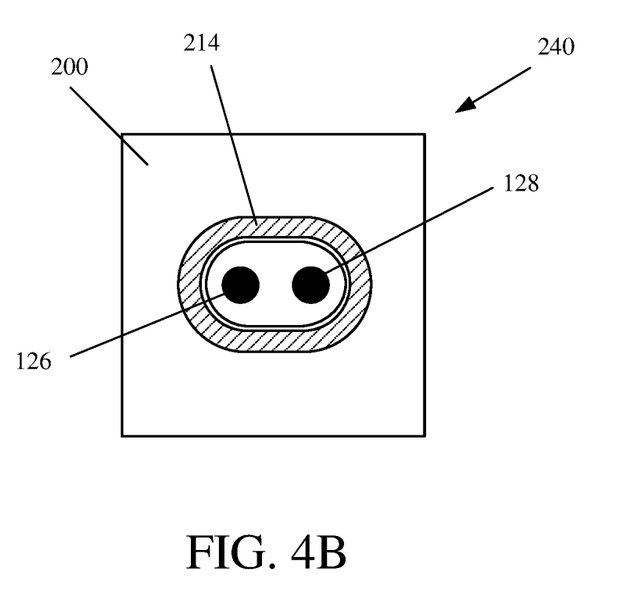

FIGS. 4A and 4B are cross-sectional side and top plan views, respectively, of a plurality of sensors mounted to a single-use bioreactor 240 through a port 204 in accordance with an embodiment of the present invention. In one embodiment, port 204 is configured to accommodate multiple sensors through a single aperture 202 in a bag wall 200. Utilizing a port such as port 204 allows for multiple sensors to be in fluidic contact with a reaction mixture within bioreactor 240 while minimizing the risk of leakage during the manufacturing process.

FIG. 4A is a cross-sectional view of a plurality of sensors disposed within a single port 204 of a single-use bioreactor bag 240 in accordance with an embodiment of the present invention. Sensors 126, 128 are generally sealed within port 204. In the example shown, sensors 126, 128 are pH sensors such as those described in U.S. Pat. No. 8,900,855. However, embodiments of the present invention can be practiced with any suitable sensors.

In one embodiment, bioreactor bag 240 comprises a bag wall 200 with an aperture 202. Aperture 202 is configured to receive a port 204. Port 204 is configured to receive any one of a variety of process variable sensors, and provide the sensor with fluidic contact to a reaction mixture within bioreactor bag 240 so the sensor can provide sensed process variable information.

In one embodiment, port 204 comprises a flange 206 that is fixedly attached to bag wall 200. In one embodiment, the fixed attachment comprises an adhesive layer 212 connected, on a first side, to bag wall 200 and, on a second side, to flange 206. In another embodiment, the fixed attachment comprises a thermal welding between flange 206 and bag wall 200 such that a portion of flange 206 is fused to bag wall 200. In one embodiment, flange 206 and bag wall 200 comprise the same material, and thermal welding comprises heating corresponding thermal welding regions 212 above their melting point such that they fuse into a single layer. In one embodiment, the fused portion creates a seal 214 that extends around the entirety of the port 204.

Embodiments described herein can thus allow a single port to accommodate a multi-sensor or a plurality of individual sensors. For example, if the port can accommodate one pH sensor and one DO sensor, instead of a manufacturing process that involves welding two ports on the bag, using two separate welding processes, only one welding process is needed. Additionally, it is expressly contemplated that the individual sensors may be activated individually, if desired. Further, in one embodiment, if one of sensor 126 or 128 is not attached, the corresponding inlet, 226 or 228 respectively, may be sealed, plugged, or otherwise closed such that reaction mixture within bioreactor bag 240 is protected from contamination and/or leakage from bag 240. Inlets 226 and 228 may, in one embodiment, comprise a one-way valve configured to allow insertion of a sensor 126 or 128 without allowing fluid from bag 240 to contact a non-sterile environment outside bag 240.

Sensors 126, 128 may sense the same variable, for example pH, or they may sense different process variables within the bioreactor 240. Sensors 126 and 128 may comprises any of: temperature sensors, pressure sensors, dissolved oxygen sensors, carbon dioxide sensors, conductivity sensors, pH sensors, colorimetric sensors, or any other suitable sensors. Sensors 126 and 128 may also be exchangeable, based on the intended reaction within bioreactor 240, and the relevant process variables for the intended reaction.

While the embodiment illustrated with respect to FIGS. 4A and 4B shows two distinct sensors 126, 128, additional sensors may be mounted within port 204 in accordance with additional embodiments of the present invention. Additionally where sensors 126, 128 are the same type, it is expressly contemplated that each of the two sensors may have a different operating characteristic or range. For example, a first pressure sensor may have a range of 0-100 PSI, while a second pressure sensor may only have a range between 5-10 PSI but may have very high accuracy and precision within the noted range.

Figure 5:
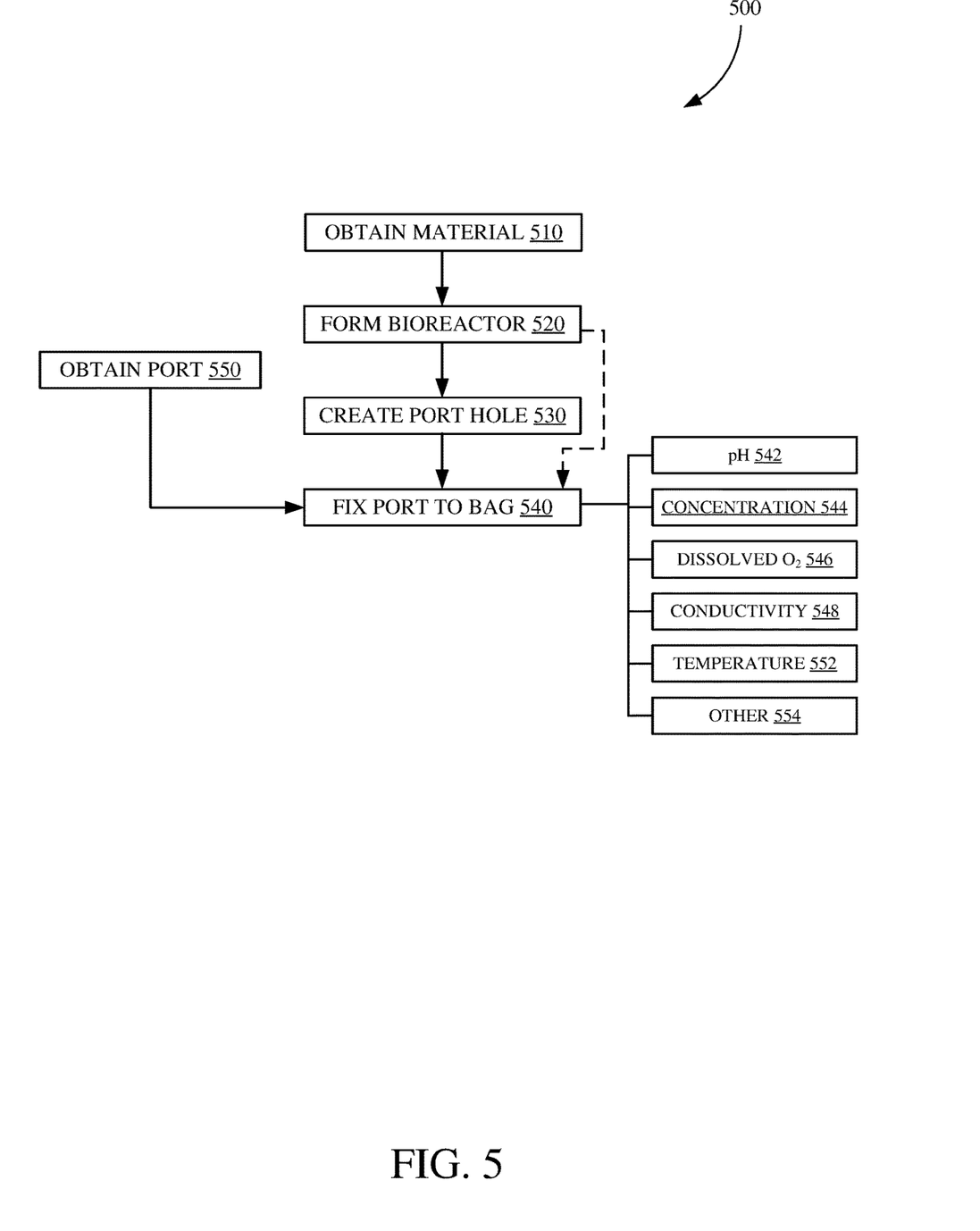
FIG. 5 illustrates an exemplary method for constructing a disposable bioreactor bag, in accordance with an embodiment of the present invention.

FIG. 5 illustrates an exemplary method for constructing a disposable bioreactor bag and sensor port, in accordance with an embodiment of the present invention. Method 500 may be used, in one embodiment, to create a bioreactor bag such as bag 40 or bag 240, described above with regard to FIGS. 1-4.

In block 510, material for the bioreactor bag is obtained. In one embodiment, the bioreactor bag is comprised of a polymer selected for properties conducive to the intended reaction conditions. For example, a bioreactor bag, such as bag 240, may be comprised of a material that is inert, or nonreactive, with any of the solvent, reactants, and/or catalysts to be used in the reaction for which the bioreactor bag is designed.

In block 520, a bioreactor bag is formed. In one embodiment, the bioreactor bag comprises a single portion of a polymeric material, for example heated and blown into the desired shape. However, other formation processes could also be used. In another embodiment, the bioreactor bag is formed of multiple polymeric material portions, connected by a plurality of seams. In one embodiment, formation of a bioreactor bag is conducted within a sterile environment such that the interior side of the bioreactor remains sterile and/or uncontaminated. In another embodiment, sterilization of the bioreactor bag comprises a separate step within method 500 and may occur either before or after a sensor port is fixed to an aperture on the wall of the bioreactor bag.

In block 530, an aperture is created within the bioreactor bag. In at least one embodiment, however, bioreactor bag is formed with an existing aperture. The aperture can be formed by removing a portion of the bag wall, for example by a hole-punching mechanism, or any other suitable mechanism.

In block 550, a port is obtained. In one embodiment, the port comprises the same material as the bioreactor bag. In another embodiment, the port comprises a different material than the bioreactor bag. In one embodiment, both the bioreactor bag and the port comprise plastic. In one embodiment, the port includes a flange configured to be placed in contact with an interior side of the bag wall. In one embodiment, the port body and the flange comprise different materials.

In block 540, the port is fixed to the bioreactor bag. A portion of the port, for example flange 206 of port 204, is fitted within the bioreactor bag such that it can be fixedly attached to the interior bag wall. In another embodiment, the port is fixedly attached to an exterior side of the bag wall. The port can be fixedly attached to the bioreactor bag utilizing an adhesive layer or utilizing a thermal welding process.

In one embodiment, the port is fixedly attached to the bioreactor bag such that any one of a plurality of sensors can be inserted into an aperture of the port and placed in contact with a reaction fluid. For example, in one embodiment, sensor information relating to any of pH 542, reactant or product concentration 544, dissolved oxygen 546, conductivity 548, temperature 552, or other relevant process variable, can be obtained through the port. In one embodiment, the port is configured to receive a multi-sensor that can provide sensor signals for a plurality of process variables. In another embodiment, the port is configured to receive multiple sensors, each configured to report sensor signals for a process variable.

Although the present invention has been described with reference to preferred embodiments, workers skilled in the art will recognize that changes may be made in form and detail without departing from the spirit and scope of the invention.

What is claimed is:
1. A bioreactor vessel comprising:
a bioreactor bag wall having an interior side and an exterior side and art aperture extending from the interior side to the exterior side, wherein the interior side is configured to contact and house a reaction mixture;
a port mounted proximate the aperture, the port including a flange fixedly attached to the bioreactor bag, such that a fluidic seal is maintained along a circumference of the flange, the port having a tubing barb to maintain tubing placed around the port;
first and second sensor inlets individually disposed in the port, the second sensor inlet disposed adjacent to and spaced individually from the first sensor inlet, each sensor inlet being configured to allow insertion of a sensor therethrough;

a first sensor disposed in and coupled to one of the first and second sensor inlets; and a second sensor disposed in and coupled to the other of the first and second sensor inlets.

2. The bioreactor vessel of claim 1, wherein the post tiredly attached attached to the interior side of the wall.

3. The bioreactor vessel claim 1, wherein the port is fixedly attached to the exterior side of the wall.

4. The bioreactor vessel of claim 2, wherein the at least one sensor comprises first and second sensors that are provided in a multi-sensor assembly.

5. The bioreactor vessel claim 1, wherein at least one sensor is configured to sense a variable selected from the group consisting of:
pH;
concentration of a reaction mixture;
dissolved oxygen concentration;
conductivity;
temperature; and,
pressure.

6. The bioreactor vessel of claim 1, wherein the interior side of the bioreactor vessel is sterile.

7. The bioreactor vessel of claim 1, wherein fixedly attached comprises an adhesive layer attached, on a first side, to the interior side of the bioreactor vessel and, on a second side, to the flange.

8. The bioreactor vessel of claim 1, wherein fixedly attached comprises a welded connection between the flange and the interior side of the bioreactor vessel.

9. The bioreactor vessel of claim 1, wherein the port and the bioreactor vessel comprise a plastic material.

10. The bioreactor vessel of claim 8, wherein the welded connection is a thermal welded connection.

11. The bioreactor vessel of claim 7, wherein the adhesive is a water-resistant adhesive, and the reaction chamber is configured to house a water-based reaction.

12. The bioreaction vessel of claim 7, wherein the adhesive is an oil-resistant adhesive, and the reaction chamber is configured to house an oil-based reaction.

13. The bioreactor vessel of claim 1, wherein the at least one sensor comprises first and second sensors configured to measure the same process variable, the first sensor having a first sensing range, and the second sensor having a second sensing range that is different than the first sensing range of the first sensor.

14. The bioreactor vessel of claim 1, wherein the port is circular.

15. The bioreactor vessel of claim 1, wherein the port is elliptical.

* * * * *